United States Patent
Usui

(10) Patent No.: US 8,369,947 B2
(45) Date of Patent: Feb. 5, 2013

(54) NERVE STIMULATION DEVICE

(75) Inventor: Takeo Usui, Tokyo (JP)

(73) Assignee: Olympus Corporation, Tokyo (JP)

( * ) Notice: Subject to any disclaimer, the term of this patent is extended or adjusted under 35 U.S.C. 154(b) by 72 days.

(21) Appl. No.: 12/885,890

(22) Filed: Sep. 20, 2010

(65) Prior Publication Data

US 2011/0118801 A1    May 19, 2011

(30) Foreign Application Priority Data

Nov. 13, 2009   (JP) .................................. 2009-259911

(51) Int. Cl.
*A61N 1/36* (2006.01)
(52) U.S. Cl. ........................................... 607/9; 607/118
(58) Field of Classification Search ............... 607/9, 118
See application file for complete search history.

(56) References Cited

U.S. PATENT DOCUMENTS

| | | | | |
|---|---|---|---|---|
| 5,199,428 A * | 4/1993 | Obel et al. | ...................... | 607/44 |
| 2003/0040774 A1 * | 2/2003 | Terry et al. | ........................ | 607/2 |
| 2003/0045909 A1 * | 3/2003 | Gross et al. | ....................... | 607/9 |
| 2006/0259084 A1 * | 11/2006 | Zhang et al. | ....................... | 607/9 |
| 2007/0021786 A1 * | 1/2007 | Parnis et al. | ........................ | 607/2 |
| 2007/0203527 A1 * | 8/2007 | Ben-David et al. | ............. | 607/14 |
| 2009/0005845 A1 * | 1/2009 | David et al. | ................... | 607/122 |
| 2010/0191311 A1 * | 7/2010 | Scheiner et al. | ................ | 607/62 |

FOREIGN PATENT DOCUMENTS

| | | |
|---|---|---|
| JP | 08-038625 | 2/1996 |
| JP | 2004-173790 | 6/2004 |

* cited by examiner

*Primary Examiner* — Carl H Layno
*Assistant Examiner* — Jennifer Ghand
(74) *Attorney, Agent, or Firm* — Scully Scott Murphy & Presser, PC

(57) ABSTRACT

To provide a nerve stimulation device capable of stimulating a vagus nerve stably while reducing the risk of interrupting a treatment by nerve stimulation due to disconnection or the like. Adopted is a nerve stimulation device including a first electrode and a second electrode disposed in different positions on the vagus nerve, a pulse generating part connected to each of these electrodes, for outputting an electric pulse for stimulating the vagus nerve, and a setting part for switching the electrode to which the electric pulse from the pulse generating part is transmitted.

4 Claims, 2 Drawing Sheets

NERVE STIMULATION DEVICE

BACKGROUND OF THE INVENTION

1. Field of the Invention

The present invention relates to a nerve stimulation device.

This application is based on Japanese Patent Application No. 2009-259911, the content of which is incorporated herein by reference.

2. Description of Related Art

Conventionally, there is known a treatment method that conducts defibrillation with energy lower than usual by stimulating a vagus nerve at the time of ventricular fibrillation of heart (convulsion condition of ventricle) (see, for example, Japanese Unexamined Patent Application, Publication No. Hei 8-38625). Japanese Unexamined Patent Application, Publication No. Hei 8-38625 also discloses installing a set of electrodes in a cervical region as an electrode for stimulating a vagus nerve.

There is known a cardiac treatment device having a set of electrodes for stimulating a vagus nerve that stimulates a vagus nerve when the cardiac rate is higher than a predetermined rate, and conducts cardiac stimulation rather than nerve stimulation when the cardiac rate is lower than the predetermined rate (see, for example, Japanese Unexamined Patent Application, Publication No. 2004-173790).

However, when contact resistance of an electrode to a nerve bundle increases with time due to adhesion of tissue or the like to the electrode, or when impedance increases due to disconnection of a lead wire or the like due to motion of living body, it is not possible to provide energy that is enough for an electric pulse to excite a nerve cell. In such a case, it may become difficult to continue the treatment of stimulating a vagus nerve with cardiac treatment devices disclosed in Japanese Unexamined Patent Application, Publication Nos. Hei 8-38625 and 2004-173790).

BRIEF SUMMARY OF THE INVENTION

The present invention adopts a nerve stimulation device including a plurality of sets of electrodes disposed in different positions on a vagus nerve, a pulse outputting unit connected to each of the plurality of sets of electrodes, for outputting a pulse for stimulating the vagus nerve, and a switching unit for switching the electrode to which the pulse from the pulse outputting unit is transmitted.

According to the present invention, the pulse outputted from the pulse outputting unit is transmitted to the plurality of sets of electrodes disposed in the different positions on the vagus nerve, and the vagus nerve is stimulated and the cardiac rate can be reduced. In this case, the electrode to which the pulse from the pulse outputting unit is transmitted is switched among the plurality of sets of electrodes by the switching unit.

As a result, it is possible to stimulate different positions on the vagus nerve, and to reduce the cardiac rate effectively, for example, by stimulating the part where the cardiac rate reducing effect is high. By using the plurality of sets of electrodes, it is possible to reduce the risk that the treatment by nerve stimulation is interrupted by disconnection or the like.

In the above invention, the switching unit may sequentially switch the electrode to which the pulse from the pulse outputting unit is transmitted.

By sequentially switching the electrode to which the pulse is transmitted, it is possible to reduce the use frequency of each electrode. As a result, it is possible to stimulate the vagus nerve in a more dispersed manner compared with the case where the vagus nerve is stimulated intensively to one site by the set of electrodes as is in the related art, and to reduce the risk of damage on a nerve tissue.

In the above invention, the switching unit may transmit the pulse from the pulse outputting unit to the plurality of sets of electrodes concurrently.

By transmitting the pulse to the plurality of sets of electrodes concurrently, it is possible to stimulate the vagus nerve continuously even when disconnection occurs in a set of electrodes or contact impedance of electrode increases due to adhesion of tissue or the like, and to reduce the risk that the treatment by nerve stimulation is interrupted.

In the above invention, a cardiac beat detecting unit for detecting a cardiac beat of a heart may be provided, and the switching unit may select at least a set of electrodes from the plurality of sets of electrodes depending on the cardiac beat detected by the cardiac beat detecting unit and transmit the pulse from the pulse outputting unit to the selected set of electrodes.

In this manner, the electrode to which the pulse from the pulse outputting unit is transmitted is switched depending on the cardiac beat detected by the cardiac beat detecting unit. In this way, the position of the vagus nerve to be stimulated by the pulse can be varied depending on the level of the cardiac rate.

In other words, in a tachycardia dangerous state where the cardiac rate is high, the cardiac rate can be largely reduced by stimulating the part where the cardiac rate reducing effect is high, and such a risk that the cardiac rate does not decrease due to short of stimulation can be reduced.

On the other hand, when the cardiac rate is low, excess stimulation can be prevented by stimulating the part where the cardiac rate reducing effect is low, so that the risk of damaging the nerve tissue and the risk of excessively decreasing the cardiac rate by excess stimulation can be reduced.

According to the present invention, the risk of interrupting the treatment by nerve stimulation due to disconnection or the like is reduced, and the vagus nerve can be advantageously stimulated in a stable manner.

DETAILED DESCRIPTION OF THE INVENTION

First Embodiment

A nerve stimulation device 1 according to a first embodiment of the present invention will be described below with reference to the drawings.

Figure 1:
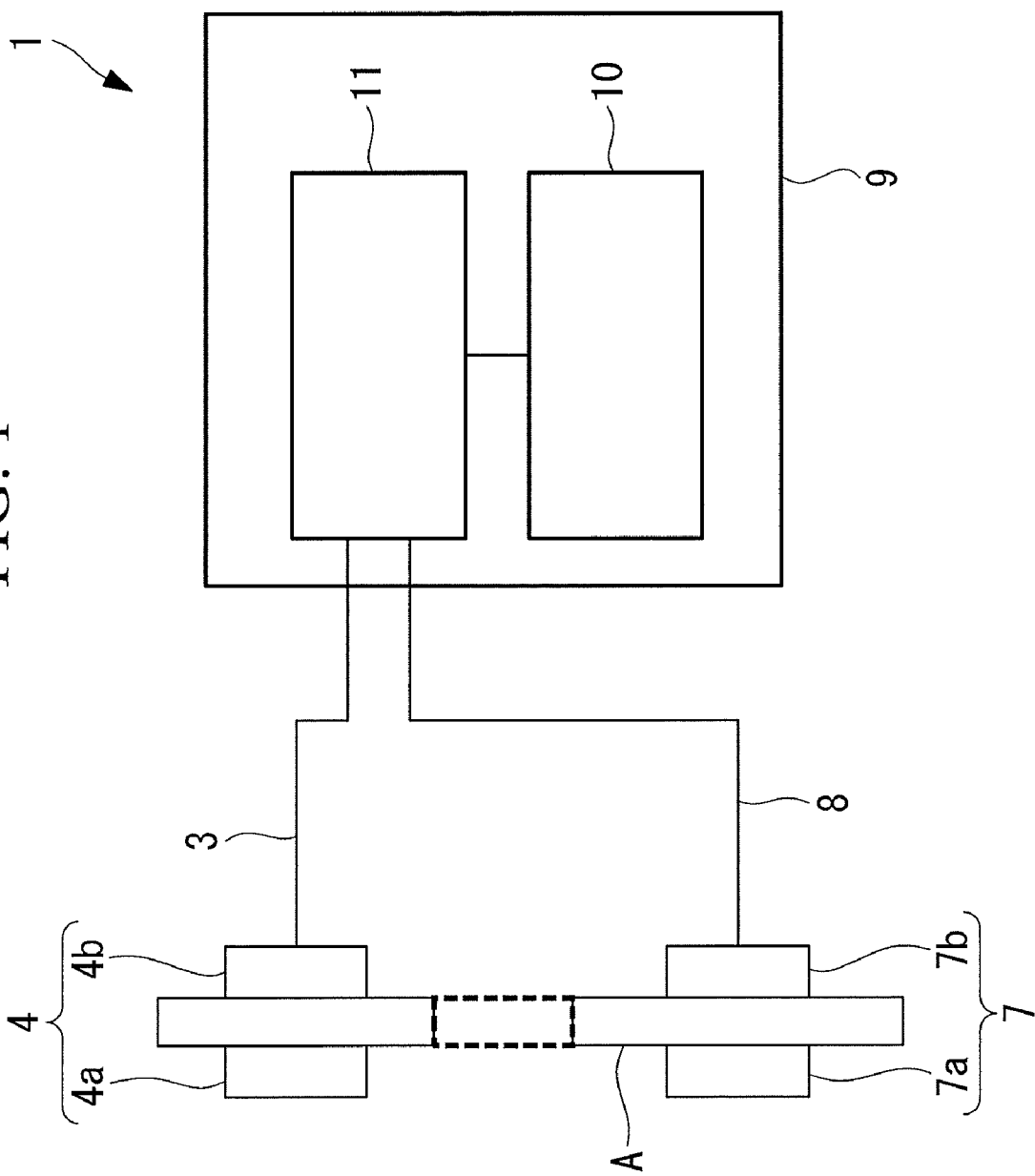
FIG. 1 is a functional block diagram of a nerve stimulation device according to a first embodiment of the present invention.

As shown in FIG. 1, the nerve stimulation device 1 according to the present embodiment is a nerve stimulation device that is implanted into a body and stimulates a vagus nerve A and includes a device main body 9, a first electrode 4 and a second electrode 7 that are attached to the vagus nerve A, a first lead 3 connecting the device main body 9 and the first electrode 4, and a second lead 8 connecting the device main body 9 and the second electrode 7.

The device main body 9 includes a pulse generating part (pulse outputting unit) 11 that outputs an electric pulse (pulse) to the first electrode 4 or the second electrode 7, and a setting part (switching unit) 10 that sets the electrode to which the electric pulse from the pulse generating part 11 is transmitted from the first electrode 4 and the second electrode 7.

The first electrode 4 has an anode electrode part 4a and a cathode electrode part 4b that are electrically insulated from each other. Each electrode part 4a, 4b is formed, for example, into a cylindrical shape, and is adapted to be attached to cover the lateral face of the vagus nerve A circumferentially. The electrode parts 4a and 4b are provided at an interval in the longitudinal direction of the vagus nerve A.

The second electrode 7 has a configuration similar to that of the first electrode 4, and has an anode electrode part 7a and a cathode electrode part 7b that are electrically insulated from each other. The first electrode 4 and the second electrode 7 are disposed in different positions on the vagus nerve A. Concretely, for example, the first electrode 4 is disposed on a vagus nerve bundle in a cervical region and the second electrode 7 is disposed on a vagus nerve bundle near an intrathoracic superior vena cava.

The pulse generating part 11 generates an electric pulse intermittently on a certain cycle, and outputs the electric pulse to each of the electrode parts 4a and 4b (or each of the electrode parts 7a and 7b) via the respective leads 3 and 8. As a result, in a position situated between the electrode parts 4a and 4b (or the electrode parts 7a, 7b), the vagus nerve A is stimulated by the electric pulse and excites so that the cardiac rate is decreased. The pulse generating part 11 increases or decreases energy of an electric pulse by lengthening or shortening a pulse width of an electric pulse to be generated, thereby enhancing or attenuating the stimulation to be given to the vagus nerve A.

The setting part 10 alternately switches the electrode to which an electric pulse from the pulse generating part 11 is to be transmitted, between the first electrode 4 and the second electrode 7 every predetermined time. The timing of switching the electrode may be, for example, every day or every hour, as can be appropriately varied by a user.

An operation of the nerve stimulation device 1 having the above configuration will be described.

The nerve stimulation device 1 according to the present embodiment is implanted into a body of a patient subjected to a cardiac treatment, and as the operation starts, the electric pulse outputted from the pulse generating part 11 is transmitted to the first electrode 4 and the second electrode 7 that are disposed in different positions on the vagus nerve A. As a result, the vagus nerve A is stimulated and the cardiac rate can be reduced.

In this case, the pulse generating part 11 is adapted to alternately output the electric pulse to the first electrode 4 and the second electrode 7 every time set in the setting part 10. As a result, the vagus nerve bundle in the cervical region on which the first electrode 4 is disposed, and the vagus nerve bundle near an intrathoracic superior vena cava on which the second electrode 7 is disposed are alternately stimulated every time set in the setting part 10.

The vagus nerve bundle starts from the brain and reaches the heart and other various organs through the cervical region and the peritoneal cavity. Nerves branched from various parts of the vagus nerve bundle run into various organs, and it is assumed that the stimulation treatment effect differs depending on the position of the stimulated nerve.

Therefore, according to the nerve stimulation device 1 of the present embodiment, it is possible to stimulate different positions on the vagus nerve A, and the cardiac rate can be reduced effectively, for example, by stimulating the part where the cardiac rate reducing effect is high.

Even when the treatment effect by the first electrode 4 and the treatment effect by the second electrode 7 are almost equivalent, for example, stimulation by the second electrode 7 disposed near the intrathoracic superior vena cava close to the heart allows a treatment at lower voltage, namely with lower energy, so that it is possible to prolong the service life of the battery-driven present device. By stimulating the vagus nerve A via an optimum electrode depending on the cause of tachycardia, it is possible to realize nerve stimulation without side effect and waste of energy consumption.

By alternately switching the electrode to which an electric pulse is transmitted, it is possible to decrease the use frequency of each electrode. As a result, it is possible stimulate the vagus nerve A in a more dispersed manner compared with the case where the vagus nerve A is stimulated intensively in one site by the set of electrodes as is in the related art, and to reduce the risk of damage on the nerve tissue.

In the nerve stimulation device 1 according to the present embodiment, the electric pulse from the pulse generating part 11 may be transmitted to the first electrode 4 and the second electrode 7 concurrently.

With this configuration, it is possible to stimulate the vagus nerve A continuously using the other electrode even when contact impedance increases due to disconnection of one of the electrodes, or adhesion of a tissue or the like, so that the risk of interrupting the nerve stimulation treatment can be reduced.

Impedances of the first electrode 4 and the second electrode 7 may be regularly checked, and when abnormality in impedance is found, it is recognized as abnormality due to disconnection of a lead or change in biological tissue, and the operation may be switched such that the electric pulse is outputted only to the other electrode without using the electrode for which abnormality is recognized.

Second Embodiment

Next, a nerve stimulation device 2 according to a second embodiment of the present invention will be described with reference to the drawings. In the description of the present embodiment, description for the point common to that of the nerve stimulation device 1 according to the first embodiment will be omitted, and description will be given mainly for different points.

The nerve stimulation device 2 according to the present embodiment differs from the nerve stimulation device 1 according to the first embodiment in that a cardiac beat detecting part for detecting a cardiac beat from a cardioelectric signal from a heart B is provided.

Figure 2:
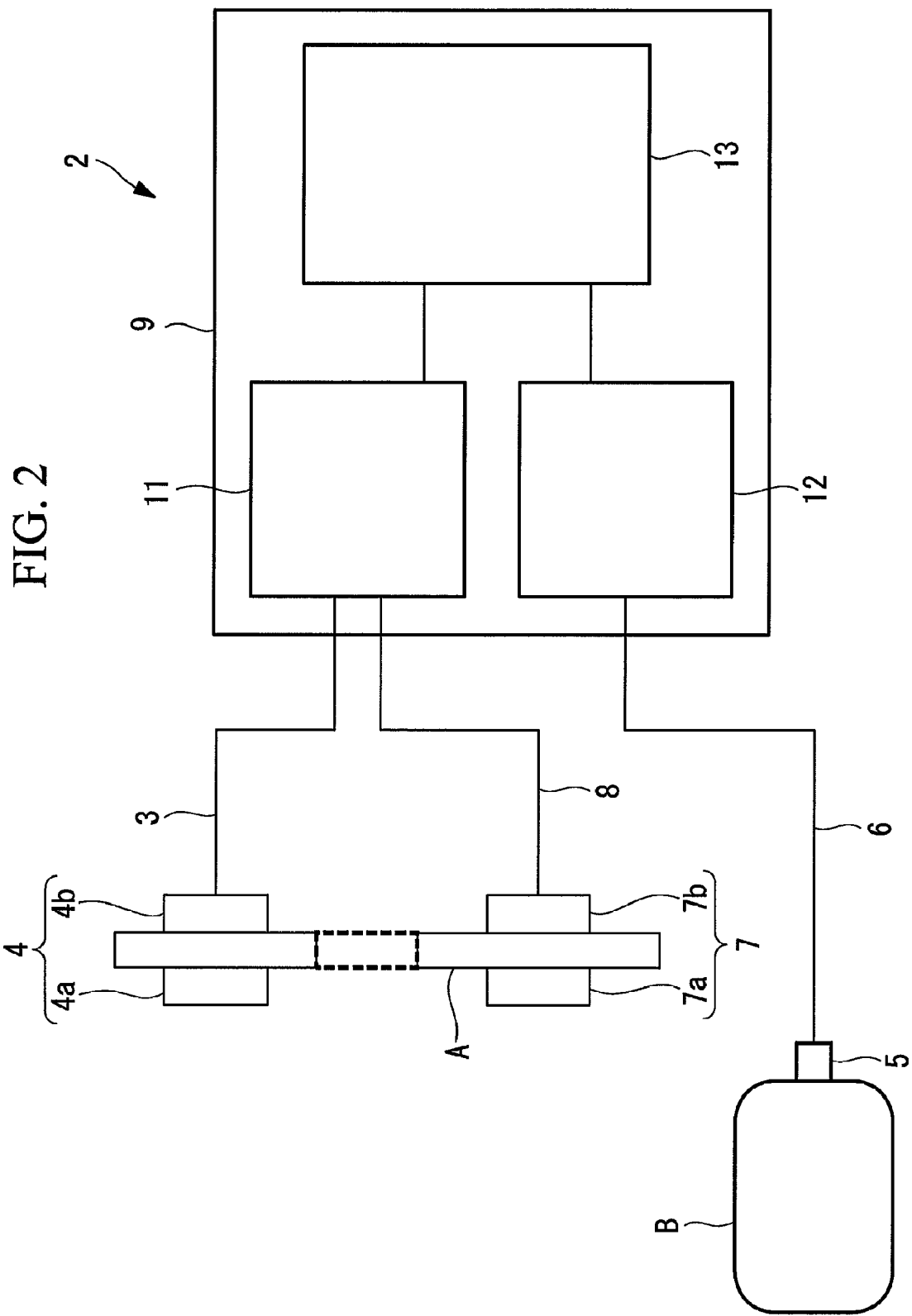
FIG. 2 is a functional block diagram of a nerve stimulation device according to a second embodiment of the present invention.

As shown in FIG. 2, the nerve stimulation device 2 according to the present embodiment includes a device main body 9, a first electrode 4 and a second electrode 7 that are attached to a vagus nerve A, a first lead 3 connecting the device main body 9 and the first electrode 4, a second lead 8 connecting the device main body 9 and the second electrode 7, a third electrode 3 attached to the heart B, and a third lead 6 connecting the device main body 9 and the third electrode 5.

As shown in FIG. 2, the device main body 9 includes a pulse generating part (pulse outputting unit) 11 that outputs an electric pulse to the first electrode 4 and the second electrode 7, a cardiac beat detecting part (cardiac beat detecting unit) 12 that detects a cardiac beat from a cardioelectric signal from the heart B detected by the third electrode 5, and a controlling part (switching unit) 13 that controls output of the electric pulse by the pulse generating part 11.

The third electrode 5 is attached, for example, to a right ventricle of the heart B, and detects a cardioelectric signal from the heart B.

The cardiac beat detecting part 12 detects, for example, a cycle of R wave that peaks in an electrocardiogram and indicates excitation condition of the ventricle as a cardiac beat, from the cardioelectric signal from the heart B detected by the third electrode 5.

The controlling part 13, for example, makes the pulse generating part 11 supply the vagus nerve A with the electric pulse intermittently on a certain cycle. The controlling part 13 selects at least one of the first electrode 4 and the second electrode 7 depending on the cardiac cycle detected by the cardiac beat detecting part 12 and transmits the electric pulse from the pulse generating part 11 to the selected electrode.

Concretely, the controlling part 13 is adapted to determine the electrode to which the electric pulse is transmitted by measuring the cardiac rate reducing effect when the vagus nerve A is stimulated by the first electrode 4 and the second electrode 7 in real time by the cardiac beat detecting part 12, and feed-back controlling the measurement result.

An operation of the nerve stimulation device 2 having the above configuration will be described below.

The nerve stimulation device 2 according to the present embodiment is implanted in a body of a patient subjected to a cardiac treatment, and upon start of the operation, the electric pulse outputted from the pulse generating part 11 is transmitted to the first electrode 4 and the second electrode 7 disposed in different positions in vagus nerve A. As a result, the vagus nerve A is stimulated and the cardiac rate can be reduced.

In this case, the controlling part 13 selects at least one of the first electrode 4 and the second electrode 7 as the electrode to which the electric pulse from the pulse generating part 11 is transmitted depending on a cardiac cycle detected by the cardiac beat detecting part 12. As a result, it is possible to change the position of the vagus nerve A stimulated by the electric pulse depending on the level of the cardiac rate.

In other words, according to the nerve stimulation device 2 of the present embodiment, in a tachycardia dangerous state where the cardiac rate is high, the cardiac rate can be largely decreased by stimulating the part where the cardiac rate reducing effect is high, and such a risk that the cardiac rate does not decrease due to short of stimulation can be reduced. On the other hand, when the cardiac rate is low, it is possible to prevent excess stimulation by stimulating the part where the cardiac rate reducing effect is low, and to reduce the risk of damaging a nerve tissue and the risk of excessively decreasing the cardiac rate due to excess stimulation.

The cardiac rate reducing effect by each electrode is measured, and when the cardiac rate reducing effect of one of the electrodes decreases, the operation may be switched so that the electric pulse is outputted only to the other of the electrodes rather than using the electrode.

With this configuration, it is possible to stimulate the vagus nerve A continuously using the other electrode even when contact impedance increases due to disconnection of one of the electrodes, or adhesion of a tissue or the like, so that the risk of interrupting the nerve stimulation treatment can be reduced.

FIRST MODIFIED EXAMPLE

As a first modified example of the nerve stimulation device 2 according to the present embodiment, cardiac rate reducing effects obtained by stimulating the electrode individually at the time of installation of each electrode may be stored in advance as a data table, and the electrode to which the electric pulse is transmitted may be determined based on this data table and a measurement result of cardiac rate by the cardiac beat detecting part 12.

Concretely, a cardiac rate is measured by the cardiac beat detecting part 12, and the electrode to which the electric pulse is transmitted is determined depending on the magnitude of the cardiac rate in the following manner.

When the cardiac rate is low, the electric pulse is transmitted to an electrode having low cardiac rate reducing effect, or to an electrode having an effect closest to the required cardiac rate reducing effect.

When the cardiac rate is high, the electric pulse is transmitted to every electrode.

With this configuration, by stimulating every position where the electrode is disposed in the tachycardia dangerous state where the cardiac rate is high, it is possible to greatly reduce the cardiac rate, and to obtain an effective cardiac rate reducing effect. Further, when the cardiac rate is low, excess stimulation can be prevented by stimulating the part where the cardiac rate reducing effect is low, so that it is possible to reduce the risk of damaging the nerve tissue and the risk of excessively decreasing the cardiac rate by excess stimulation.

In the present modified example, the electrode to which the electric pulse is transmitted may be determined in the following manner.

When the cardiac rate is low, the electric pulse is transmitted to the electrode where the cardiac rate reducing effect is low.

When the cardiac rate is high, the electric pulse is transmitted to the electrode where the cardiac rate reducing effect is high.

In this manner, it is possible to reduce the cardiac rate stably while suppressing damage on the nerve tissue.

SECOND MODIFIED EXAMPLE

As a second modified example of the nerve stimulation device 2 according to the present embodiment, a third lead 6 may be disposed so that cardiac beat detection can be conducted both for the heart atrium and the heart ventricle, and the electrode to which the electric pulse is transmitted may be determined by the cardiac beat detecting part 12 while the atrial tachycardia and ventricular tachycardia are distinguished from each other.

Since which one of the nerve stimulations on the cervical region and near the superior vena cava is more effective for the atrial and ventricular cardiac rate reduction differs depending on the individual and the disease condition, to which one of the electrodes the electric pulse is transmitted in the case of atrial tachycardia and ventricular tachycardia is set according to a physiological test conducted at the time of introduction into a body.

In this manner, it is possible to conduct nerve stimulation via an optimum electrode depending on the cause of tachycardia, and to achieve efficient nerve stimulation while reducing the risk of damaging the nerve tissue and the risk of excessively decreasing the cardiac rate by excess stimulation.

In the above, embodiments of the present invention have been specifically described with reference to the drawings, however, concrete configurations are not limited to these embodiments, and modifications in design and the like without departing from the scope of the present invention are also included.

For example, in the present embodiment, the example that two sets of electrodes are disposed on the vagus nerve A is described, however, three or more sets of electrodes may be disposed as far as an electrode to which a pulse is selectively transmitted from a plurality of electrodes can be determined.

The electric pulse outputted to the vagus nerve A may include one pulse or a plurality of pulses.

What is claimed is:

1. A nerve stimulation device comprising:
a plurality of sets of electrodes disposed in different positions on a vagus nerve;
a pulse outputting unit connected to each of the plurality of sets of electrodes, for outputting a pulse for stimulating the vagus nerve;
a switching unit for switching the electrode to which the pulse from the pulse outputting unit is transmitted and;
a cardiac beat detecting unit for detecting a cardiac beat of a heart,
wherein the switching unit selects at least one set of electrodes from the plurality of sets of electrodes on the basis of the cardiac beat and a level of a cardiac rate detected by the cardiac beat detecting unit and transmits the pulse from the pulse outputting unit to the selected at least one set of electrodes; and
wherein the switching unit stores in a data table of the cardiac rate reducing effects obtained by stimulating the vagus nerve using the electrodes individually at the time of installation of each electrode, and determines at least one set of electrodes, to which the electric pulse is transmitted, from the plurality of sets of electrodes on the basis of the data table and a measurement result of cardiac rate by the cardiac beat detecting unit.

2. The nerve stimulation device according to claim 1, wherein the cardiac beat detecting unit detects a cardiac rate reducing effect by each of the electrodes, and
the switching unit switches from the electrodes to another when the cardiac rate reducing effect of the one of the electrodes is decreased so that the electric pulse is outputted to the another of the electrodes rather than to the one of the electrodes.

3. The nerve stimulation device according to claim 1, wherein the switching unit selects an electrode having low cardiac rate reducing effect, or an electrode having an effect closest to the required cardiac rate reducing effect from the plurality of sets of electrodes when the cardiac rate is low, and
the switching unit selects all the electrodes from the plurality of sets of electrodes when the cardiac rate is high.

4. The nerve stimulation device according to claim 1, wherein the cardiac beat detecting unit distinguishes an atrial tachycardia and a ventricular tachycardia from each other, and
the switching unit selects at least one set of electrodes from the plurality of sets of electrodes.

* * * * *